United States Patent [19]
Bachir

[11] Patent Number: 5,660,186
[45] Date of Patent: Aug. 26, 1997

[54] SPIRAL BIOPSY STYLET

[75] Inventor: Joseph S. Bachir, Ladysmith, Wis.

[73] Assignee: Marshfield Clinic, Marshfield, Wis.

[21] Appl. No.: 480,401

[22] Filed: Jun. 7, 1995

[51] Int. Cl.⁶ .................................................. A61B 10/00
[52] U.S. Cl. ..................................... 128/749; 128/754
[58] Field of Search ............................. 128/754, 755, 128/751, 898, 749

[56] References Cited

U.S. PATENT DOCUMENTS

| | | | |
|---|---|---|---|
| 769,829 | 9/1904 | Mott | 606/171 |
| 2,426,535 | 8/1947 | Turkel | 128/754 |
| 3,630,192 | 12/1971 | Jamshioi | 128/754 |
| 3,850,158 | 11/1974 | Elias et al. | 128/754 |
| 3,945,375 | 3/1976 | Banko | 606/170 |
| 4,142,517 | 3/1979 | Stavropoulos et al. | 606/179 |
| 4,337,773 | 7/1982 | Raftopoulos et al. | 128/754 |
| 4,461,305 | 7/1984 | Cibley | 606/180 |
| 4,844,064 | 7/1989 | Thimsen et al. | 128/305 |
| 5,007,917 | 4/1991 | Evans | 606/180 |
| 5,040,542 | 8/1991 | Gray | 128/754 |
| 5,106,364 | 4/1992 | Hayafuji et al. | 604/22 |
| 5,250,035 | 10/1993 | Smith et al. | 604/164 |
| 5,341,816 | 8/1994 | Allen | 128/154 |
| 5,456,267 | 10/1995 | Stark | 128/898 |

FOREIGN PATENT DOCUMENTS

| | | | |
|---|---|---|---|
| 1604361 | 11/1990 | U.S.S.R. | 128/754 |

*Primary Examiner*—Max Hindenburg
*Assistant Examiner*—Pamela L. Wingood
*Attorney, Agent, or Firm*—DeWitt Ross & Stevens SC

[57] ABSTRACT

A bioptic device of the cannula and internal stylet type wherein the stylet includes a sharp tip with a gutter adjacent to the tip for obtaining a tissue sample within a larger body of tissue. The cannula, stylet tip, and gutter bear threading to better enable the bioptic device to fix tissue when the bioptic device is rotationally advanced within the body of tissue. The cannula and stylet may additionally bear complementary threading to ensure that they can only be rotationally actuated with respect to each other.

24 Claims, 5 Drawing Sheets

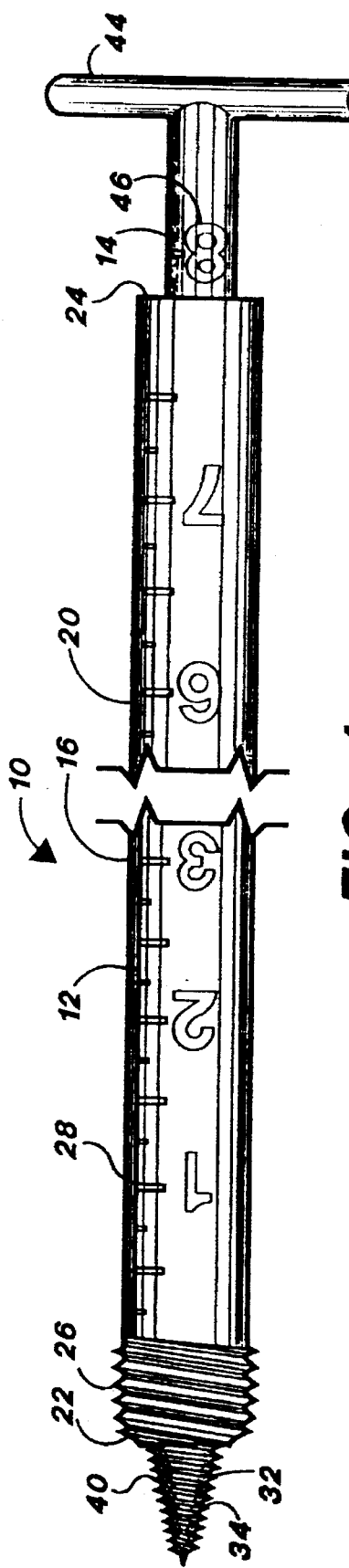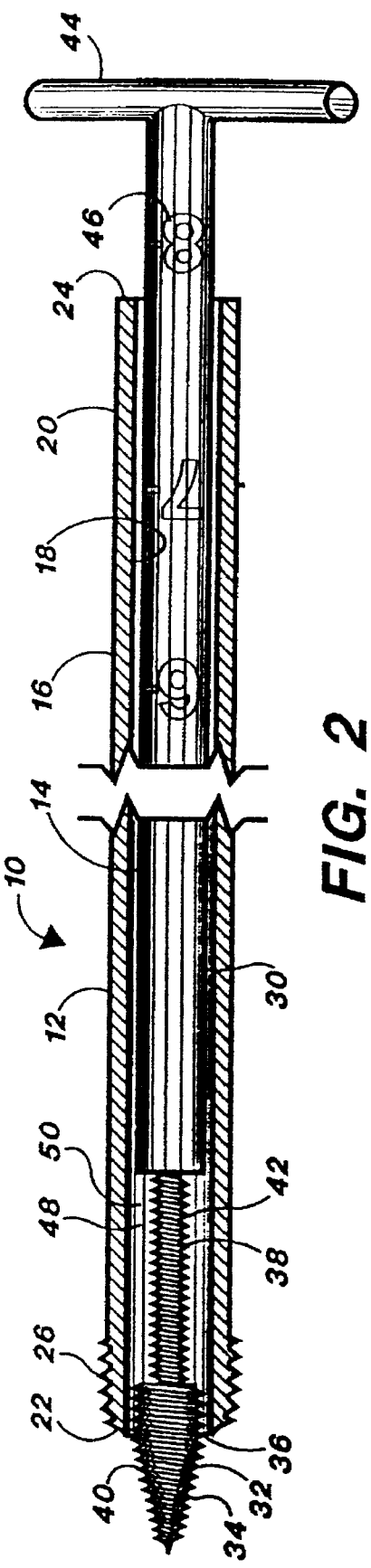

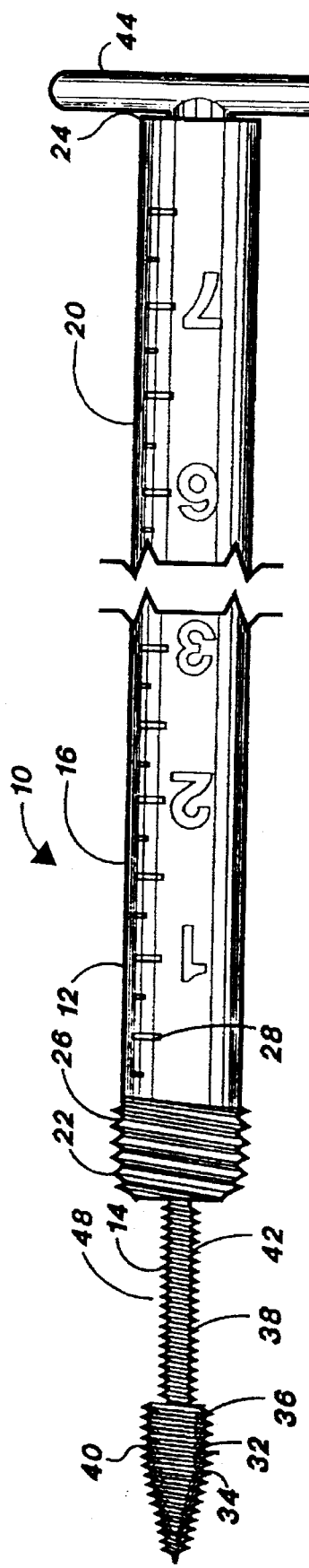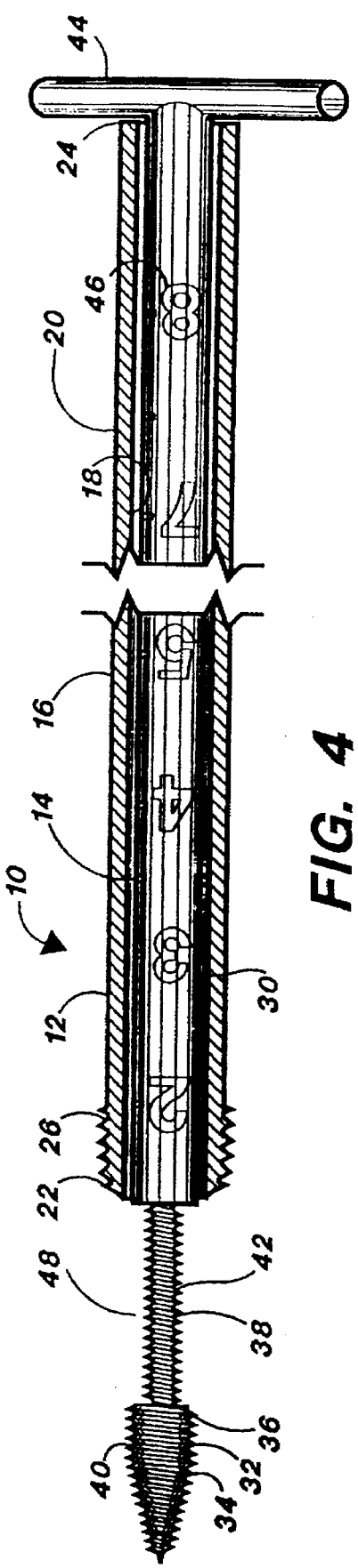
FIG. 3
FIG. 4

SPIRAL BIOPSY STYLET

FIELD OF THE INVENTION

The present invention relates generally to bioptic devices, and specifically to a rotationally-operated cannula and stylet bioptic device.

DESCRIPTION OF THE PRIOR ART

Medical personnel frequently use a biopsy to obtain tissue samples from the interior of human or animal bodies so that the tissue samples obtained in vivo may then be analyzed in vitro. The tissue sample can be analyzed by diagnostic procedures known to the art to determine certain characteristics and features of the whole body or part of the larger body of tissue.

Various types of bioptic devices have been employed for the purpose of extracting a sample of tissue for testing and other purposes. In general, bioptic devices may be classified as hard tissue bioptic devices, which are used for bone biopsies, and soft tissue bioptic devices, which are used to obtain samples of soft tissue. Bioptic devices can further be categorized as to their structure and operation. One type of bioptic device is the cannula and stylet type, wherein a tubelike cannula with a stylet resting coextensively within is inserted within the body. After the device is inserted within the body, the stylet is either actuated to obtain a tissue sample, or else the stylet is removed and replaced with a second stylet which is specially adapted to obtain a tissue sample of some sort. Examples of cannula and stylet bioptic devices are disclosed in U.S. Pat. No. 4,142,517 to Stavropoulos et al., U.S. Pat. No. 3,587,560 to Glassman, U.S. Pat. No. 4,010,737 to Vilaghy et al., U.S. Pat. No. 5,341,816 to Allen, U.S. Pat. No. 4,461,305 to Cibley, and U.S. Pat. No. 5,250,035 to Smith et al.

An exemplary soft tissue cannula and stylet bioptic device is sold by Boston Scientific Corporation under the trademark "ASAP". This bioptic device has a tubular cannula with a sharp leading edge and a rodlike internal stylet with a sharp tip. The stylet rests closely within the interior of the cannula and may slide within the cannula. A section of the stylet immediately beneath the stylet tip is cut away above a plane parallel to the axis of the stylet to define a gutter in the shape of an elongated beam having an arcuate face and a flat face. To obtain a tissue sample, the cannula and stylet are inserted coextensively within the patient's body. The stylet is then advanced independently of the cannula so that the gutter rests adjacent to or within the soft tissue to be sampled. The soft tissue then flows into the vacant gutter. The cannula is then advanced over the gutter, severing the tissue within the gutter from the surrounding tissue and enclosing the tissue within a bioptic chamber bounded by the surfaces of the gutter and the interior surface of the cannula. When the cannula is completely extended over the gutter, the bioptic sample will be secured within the bioptic chamber, and the bioptic device can then be withdrawn from the patient's body. The cannula is then withdrawn from the stylet to expose the tissue sample so that it may be removed for testing and analysis. The apparatus includes spring-loaded triggers so the cannula and stylet may be cocked and the entire bioptic procedure, save for the initial insertion and the final withdrawal of the device, may be performed by actuating the triggers.

Unfortunately, the cannula and stylet soft tissue bioptic devices of the prior art suffer from one or more defects.

Initially, the prior art cannula and stylet bioptic devices require actuation by use of a pushing or thrusting motion wherein the bioptic device is pushed to drive it into the tissue to be sampled. There are several problems with this type of actuation.

First, it can result in bending of the stylet of the bioptic device near the gutter, where the stylet has a decreased diameter and is more prone to failure due to bending forces.

Second, where there are variations in the density of the soft tissue near the area to be sampled, e.g., in the case of a "mobile" lesion where a dense tumor is surrounded by softer tissue, the pushing action is ineffectual to drive the tip of the bioptic device into the tumor. Instead, the tip of the bioptic device pushes the tumor out of the way and penetrates soft tissue resting adjacent to the tumor. As an example, it is extremely difficult to sample a lesion such as an enlarged lymph node resting on the omentum because efforts to push the tip of the bioptic device into the lesion merely push the omentum out of the path of the bioptic device. As another example, it is extremely difficult to sample a hard tumor in a female breast because efforts to insert the tip of the bioptic device into the tumor merely push the hard tumor sideways within the breast. Not only does this result in injury to the surrounding tissue, but it can also result in testing of the surrounding soft tissue in the belief that it is the dense tissue of interest. This can lead to false negative test results and the need to perform an incisional or excisional bioptic operation. This problem of tissue fixation and penetration, wherein the bioptic device cannot locate and fix the tissue to be sampled, is one of the fundamental drawbacks of the prior art bioptic devices.

Third, where the operator is unable to penetrate dense tissue because the bioptic device merely pushes it around within the body, the operator is often forced to try to penetrate the tissue to be sampled by thrusting the stylet forward with great speed and force in an attempt to stab into the dense tissue. This can be extremely painful to the patient, and if penetration of the dense tissue is unsuccessful, surrounding tissue may be accidentally injured. Such actuation also results in inaccurate test results because the operator of the bioptic device generally cannot accurately locate the bioptic device at the proper depth within the tissue of interest by use of a rapid thrusting motion.

Fourth, it is generally quite easy for an operator to injure himself or herself with a bioptic device that requires pushing or thrusting for actuation. This is because such devices must necessarily have extremely sharp tips and are generally elongated, needle-like devices, and mishandling or careless handling of the bioptic device can result in accidental puncture wounds to the operator or patient. This is a special concern to medical personnel due to the possibility of contact with the Human Immunodeficiency Virus (HIV) or the serum (type-B) hepatitis virus. The possibility of accidental stabbing or puncture wounds is also a particular concern with the automatically actuated (e.g., spring-loaded) bioptic devices of the prior art. When triggered, these devices operate with substantial speed and force, and an accidental discharge of the device could unintentionally remove a tissue sample from a patient or medical personnel.

Another disadvantage of the prior art bioptic devices is that they generally cannot obtain a large tissue specimen. Initially, this is due to physical restraints on the size of the gutter. The size of the stylet and gutter cannot be enlarged indefinitely because a large bioptic device cannot be comfortably inserted within the body. Additionally, the gutters of the prior art bioptic devices are often of small size simply because an enlarged gutter may weaken the stylet to the point where it could bend or break at the gutter, making it difficult to remove the tip of the stylet from the patient's body.

The size of the tissue samples is also limited by inherent operational drawbacks in the cannula and stylet bioptic devices of the prior art. First, soft tissue, regardless of its density, often enters the gutter only slightly when the stylet enters the desired tissue (if it enters the gutter at all). As a result, the biopsy chamber often contains little or no tissue when the cannula is advanced over the stylet. This is especially common where the tissue to be sampled is a dense tumor since the dense tissue of the tumor will usually not flow into the gutter at all. In this case, repeated insertion of the bioptic device is necessary to try to obtain a tissue sample. This can cause both extreme physical and emotional pain and greater trauma to surrounding tissue. Second, unless the leading edge of the cannula is extremely sharp, it can push tissue out of the gutter rather than severing it as the cannula is advanced over the stylet. This occurs because the leading edge of the cannula attempts to apply a compression-style cut to the tissue, i.e., the leading edge is moved solely in the direction of cutting. The leading edge therefore has a tendency to push forward the tissue to be cut as a cutting force is applied. This is to be contrasted with a shear-style cut, wherein the cutting edge is moved at a right angle to the direction of cutting as well as in the direction of cutting (i.e., a sawing motion is used).

A further disadvantage of the cannula and stylet devices of the prior art is that the operational steps required for their use are such that mistakes in operation frequently occur. The operational steps must be performed in a certain order, and unless this order is precisely followed, the tissue sample within the biopsy chamber will either be very small or nonexistent. More precisely, the step of cutting the tissue sample from the surrounding tissue must be performed by advancing the cannula over the stylet and gutter, rather than by retracting the stylet from the cannula until it rests within the cannula. The latter mode of operation, which often occurs in the hands of inexperienced users, fails to yield a tissue sample because the retraction of the stylet empties it of tissue before the leading edge of the cannula severs this tissue.

Additionally, it is not uncommon for even experienced users to sometimes erroneously follow this series of steps without realizing it. For this reason, many of the prior art bioptic devices incorporate automatic actuation features (such as spring-loaded actuation) so that the necessary order of operational steps must necessarily be followed.

Accordingly, there is a need in the art for a bioptic device which overcomes these and other disadvantages of the prior art bioptic devices.

SUMMARY OF THE INVENTION

The bioptic device of the present invention comprises a cannula including a sharp leading edge and a stylet adapted to fit within the cannula. The stylet includes a stylet tip with threading on at least a portion of the stylet tip, a stylet neck adjacent the stylet tip, and a stylet body adjacent the stylet neck, wherein the stylet neck has a smaller diameter than the stylet tip and stylet body.

The bioptic device of the present invention further comprises a cannula including a sharp leading edge and a stylet adapted to fit within the cannula. The stylet includes a stylet tip, a threaded stylet neck adjacent the stylet tip, and a stylet body adjacent the stylet neck, wherein the stylet neck has a smaller diameter than the stylet tip and stylet body.

The bioptic device of the present invention additionally comprises a cannula including a threaded leading edge and a stylet adapted to fit within the cannula, wherein the stylet includes a sharpened stylet tip, a stylet neck adjacent the stylet tip, and a stylet body adjacent the stylet tip, wherein the stylet neck has a smaller diameter than the stylet tip and stylet body.

The bioptic device of the present invention solves the problem of tissue fixation and penetration encountered in the bioptic devices of the prior art by the use of threading and rotational actuation of the bioptic device. By incorporating threading on the cannula and/or stylet and by rotationally advancing the cannula and stylet upon the tissue to be sampled, the threading grasps and fixes the tissue to be sampled so that the tissue cannot move as the bioptic device is advanced. Since the cannula is rotated as it is advanced to sever the tissue, the leading edge of the cannula applies a shear-style cut, rather than a compression-style cut, which helps to apply a surer cut with less pushing or compression of the tissue to be sampled. Also, the rotational shear-style cutting used in the present invention is slower and surer than the compression-style cutting used in the prior art bioptic devices, which requires a thrusting or pushing motion of the bioptic device to obtain a sample.

The threading on the cannula and/or stylet also helps to prevent accidental injury to the operator of the bioptic device. The threading on the cannula and/or stylet of the present invention provides resistance to direct thrusting or pushing of the bioptic device into tissue, whereas the sharp, smooth bioptic devices of the prior art can quite easily be accidentally driven into the operator's flesh by a substantial distance. It is also safer insofar as it does not require spring-loading for proper operation or easy actuation.

An additional advantage of the bioptic device of the present invention is that for the same size of cannula and stylet, larger tissue samples can be obtained than the prior art devices. Prior art gutters are limited in size because the gutter is formed by removing stylet material along one side of the stylet, and the removal of material tends to weaken the stylet. As the gutter is enlarged by removing more stylet material, there is a greater danger that the stylet will bend and/or break within the patient's body because the thrusting or pushing action used to operate the bioptic devices of the prior art subjects the stylet to bending forces. If the gutter is formed by radially decreasing the diameter of a portion of the stylet rather than by cutting away a portion of the stylet above a plane parallel to its axis, an annular bioptic chamber is formed. Since the portion of the stylet adjacent to the gutter is rodlike, rather than beamlike, it is not as susceptible to bending forces and is not as likely to bend or break when it is inserted within the body. Additionally, by including threading along the portion of the stylet that defines the gutter, the effective diameter of the stylet is increased and its strength is enhanced. Depending on the diameter of this threading, a spiral-shaped tissue sample can be obtained, and this tissue sample can be extended to a substantial length for easier examination to provide more histological information.

The bioptic device may also include complementary threading on the outer surface of the stylet and the inner surface of the cannula so that the stylet can only be rotationally advanced in relation to the cannula. This helps to ensure that the cannula can only be rotationally actuated with respect to the stylet and that the operational steps for using the bioptic device are properly followed. It also ensures that the leading edge of the cannula will apply a shear-style cut.

The bioptic device of the present invention can be used to remove a tissue specimen, or if the bioptic device is the correct size, it can be used to remove a tumor or a lesion entirely.

Further advantages, features, and objects of the invention will be apparent from the following detailed description of the invention in accompaniment with the drawings.

BRIEF DESCRIPTION OF THE DRAWINGS

FIG. 1 is a side elevational view of the bioptic device of the present invention shown with the stylet in the retracted position.

FIG. 2 is a side elevational view of the bioptic device of FIG. 1 shown with the cannula in cross-section to reveal the stylet within.

FIG. 3 is a side elevational view of the bioptic device of FIG. 1 with the stylet shown in the extended position.

FIG. 4 is a side elevational view of the bioptic device of FIG. 3 shown with the cannula in cross-section to reveal the stylet within.

DETAILED DESCRIPTION OF THE INVENTION

Figure 5:
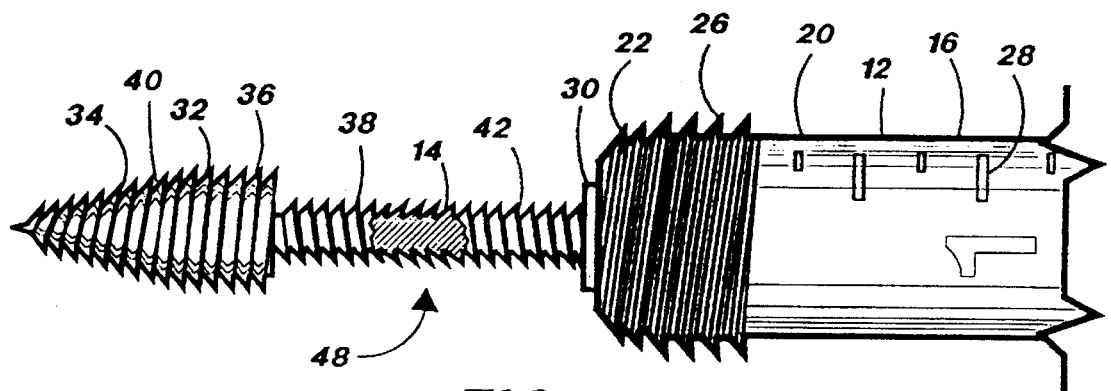
FIG. 5 is a side elevational view of the bioptic device of the present invention illustrating the use of undercut buttress threading on the cannula and stylet, wherein a portion of the stylet neck is cut away to reveal a cross-section of the neck.

With reference to the drawings, wherein the same or similar features are identified with the same reference numbers throughout, the bioptic device of the present invention is shown generally at 10. The bioptic device 10 includes a cannula 12 and a stylet 14. The cannula 12 is a hollow generally tubular member wherein the stylet 14 rests and within which the stylet 14 may be extended and retracted. The cannula 12 includes a body 16 with an interior surface 18 and exterior surface 20, a sharp leading edge 22, and an opposing end 24. The leading edge 22 includes threading 26. The body 16 may also bear distance indicia 28 which indicate the distance along the body 16 from the leading edge 22.

The stylet 14, which is best shown in FIGS. 2 and 4, includes a body 30 and a tip 32 which includes a conic tip section 34 and a cylindrical tip section 36. The cylindrical tip section 36 and the body 30 fit within the cannula 12 closely adjacent to the interior surface 18 of the cannula 12. A neck 38 bridges the tip 32 and the body 30, and has a lesser diameter than both the body 30 and the cylindrical section 36 of the stylet tip 32. As illustrated in FIGS. 1-4, the stylet tip 32 bears threading 40 and the stylet neck 38 also bears threading 42. The stylet body 30 may include a handle 44 at its end to assist in actuation of the stylet 14 within the cannula 12, and it may also include distance indicia 46 indicating the distance along the stylet body 30 from the stylet tip 32.

The annular region surrounding the stylet neck 38 and bounded by the stylet tip 32 and the stylet body 30 forms a gutter 48, wherein a tissue sample is located just before it is severed from the main body of tissue. For this reason, it is preferable that the stylet neck 38 will be fully exposed when the stylet 14 is extended from its retracted position, as shown in FIGS. 1 and 2, to its extended position, as shown in FIGS. 3 and 4, so that the gutter 48 can be fully exposed. When the cannula 12 is advanced over the gutter 48, as shown in FIG. 2, a biopsy chamber 50 is defined by the gutter 48 and the interior surface 18 of the cannula 12.

The operation of the bioptic device 10 shown in FIGS. 1-4 proceeds as follows. First, the bioptic device 10 is actuated so that the stylet 14 is in the retracted position, as shown in FIGS. 1 and 2. The bioptic device 10 is introduced into the patient's body by inserting the tip 32 of the stylet 14 into the body near the tissue to be sampled. The entire bioptic device 10 is then rotated so that the threading 40 on the stylet tip and the threading 26 on the leading edge 22 of the cannula 12 drives the bioptic device 10 within the patient's body.

When the stylet tip 32 encounters the tissue to be sampled, it will penetrate it rather than pushing it aside because the threading 40 applies a shear-style cut upon entering the tissue to be sampled rather than a compressive-style cut, as the bioptic devices of the prior art do. In other words, rather than merely trying to push into and puncture the tissue to be sampled with the sharp tip 32 of the stylet 14, the threading 40 will cut into and grasp the tissue to be sampled rather than merely pushing it in an effort to gain entry.

As the bioptic device 10 is continually rotated, the leading edge 22 of the cannula 12 will enter the tissue to be sampled as well. When this is done, the leading edge 22 of the cannula 12 will also be firmly anchored to the tissue to be sampled due to its threading 26.

The operator may then rotate the stylet 14 independently of the cannula 14, driving the stylet 14 deeper into the tissue to be sampled. This will gradually result in the exposure of the gutter 48, as shown in FIGS. 3 and 4. As this occurs, the tissue to be sampled flows into the gutter 48. The threading 42 on the stylet neck 38 grips the tissue so that the leading edge 22 of the cannula 12 will not displace the tissue from the gutter 48 when the cannula 12 is advanced.

The cannula 12 may then be rotationally advanced so that the sharp leading edge 22 severs the tissue within the gutter 48 from the remaining body of tissue. Since the cannula 12 is advanced rotationally, the sharp leading edge 22 severs the tissue using a shear-style cut, rather than a compression-style cut. This prevents the leading edge 22 from pushing the tissue out of the gutter 48 and from compressing the tissue when cutting proceeds. Therefore, only tissue along the cut line is injured, and surrounding tissue is not traumatized by compression.

When the cannula 12 is fully advanced and the tissue sample is secured within the bioptic chamber 50, the bioptic device 10 may be rotated in the opposite direction to withdraw it from the patient's body. When the bioptic device 10 is fully withdrawn, the cannula 12 may again be retracted independently of the stylet 14 so that the tissue sample may be removed for analysis.

Alternatively, instead of withdrawing the bioptic device 10 from the body, it may be left within the patient's body after the tissue sample is secured within the biopsy chamber 50, and the stylet 14 alone may be withdrawn from the cannula 12. The tissue sample may be removed from the withdrawn stylet 14, and hemostatic material may be inserted within the end 24 of the cannula 12 and pushed through the length of the cannula 12 and finally within the wound caused by the removal of the tissue sample. The cannula 12 may then be rotated to effect its removal.

During the preceding steps, distance indicia 28 on the cannula 12 and distance indicia 46 on the stylet 14 assist the operator in determining how far the bioptic device 10 has advanced within the body.

A significant advance is gained over the devices of the prior art merely by advancing the cannula 12 by use of a rotating motion. By doing so, the tissue within the gutter 48 is severed by use of a shear-style cut rather than a compression-style cut. This prevents the cannula 12 from pushing the tissue to be sampled out of the gutter 48. Also, a shear-style cut reduces the amount of trauma to surrounding tissue because it does not compress and injure the tissue near the area to be cut. Additionally, unlike a compressive-style cut, a shear-style cut will not compress and damage the tissue sample.

FIGS. 5-9 illustrate alternative embodiments of the bioptic device of the present invention. It is contemplated that the several features and modifications shown in these alternate embodiments may be combined in different ways to craft bioptic devices 10 which satisfy particular needs or unique functions in the field of bioptic sampling.

FIG. 5 illustrates an embodiment which uses undercut buttress threading, the preferred type of threading, for the cannula threading 26 and the stylet tip and neck threading 40 and 42. It is understood that the threading utilized on the bioptic device 10 may take the form of any type of threading known to the prior art, such as American National threading, unified (external) threading, metric threading, sharp V threading, Whitworth's standard threading, Acme threading, knuckle threading, square threading, or standard worm threading. However, preferred types of threading have higher grasping power on the tissue they engage. One preferred type of threading is buttress threading, wherein the forward sides of the threading are angled opposite the direction of advancement of the threaded article. Also preferred are threading types which are undercut so that the rear sides of the threading are also angled opposite the direction of advancement of the threaded article, i.e., the rear side of the thread defines a trough. Because undercut threading exerts a force in a radially inward direction on the tissue that it grasps, it provides extremely effective grasping forces on the cannula 12 and stylet 14, especially when used in conjunction with buttress threading. Such threading is especially valuable on the gutter 48 because it pulls the tissue to be sampled into the gutter 48 and ensures that tissue is present for sampling.

Figure 6:
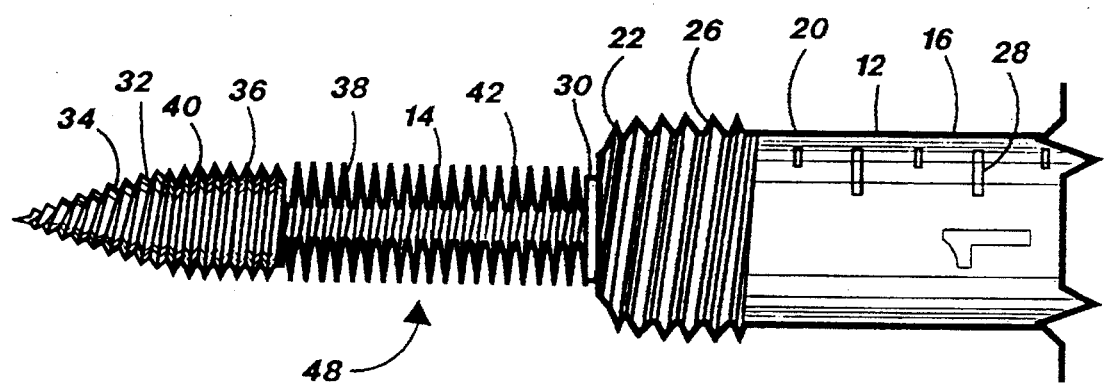
FIG. 6 is a side elevational view of an alternative embodiment of the bioptic device of the present invention wherein the threading on the neck adjacent the gutter has the same major diameter as the threading on the stylet tip.

FIG. 6 illustrates an alternative embodiment wherein the threading 42 on the stylet neck 38 has a major diameter substantially equal to the diameter of the cylindrical section 36 of the stylet tip 32 and the stylet body 30. This embodiment has the advantage that the wide-diameter threading 42 imparts substantial strength to the stylet neck 38 to enable it to resist bending. A tissue sample of substantial volume is still obtained because the tissue sample located within the gutter 48 is in the shape of a spiral. The spiral tissue sample may be extended to substantial length during later analysis, making the examination of the tissue sample easier and allowing more information about the tissue sample to be obtained.

Figure 7:
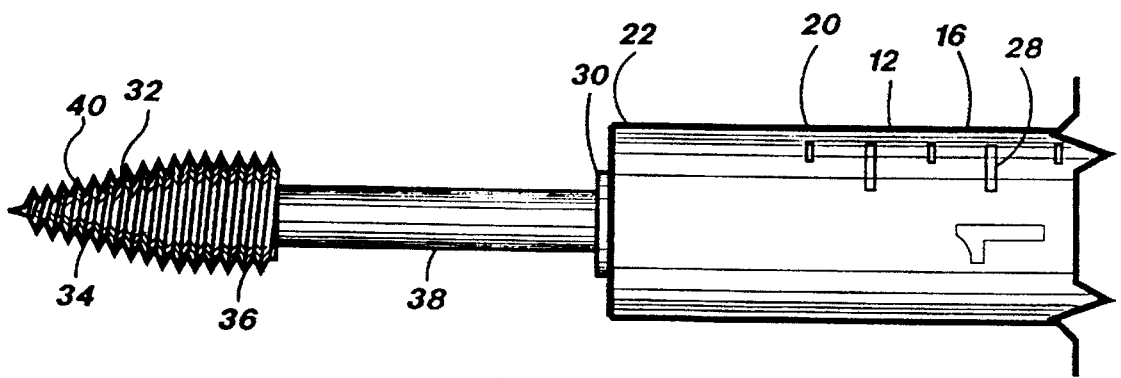
FIG. 7 is a side elevational view of a second alternative embodiment of the bioptic device of the present invention wherein only the stylet tip bears threading.

FIG. 7 illustrates an alternative embodiment wherein only the stylet tip 32 bears threading 40. The threading 40 allows the stylet tip 32 to fix the tissue to be sampled as the stylet 14 is rotationally advanced. The cannula 12 does not include threading and thus does not fix the tissue, and it may be advanced either by merely pushing it forward or by rotationally advancing it.

Figure 8:
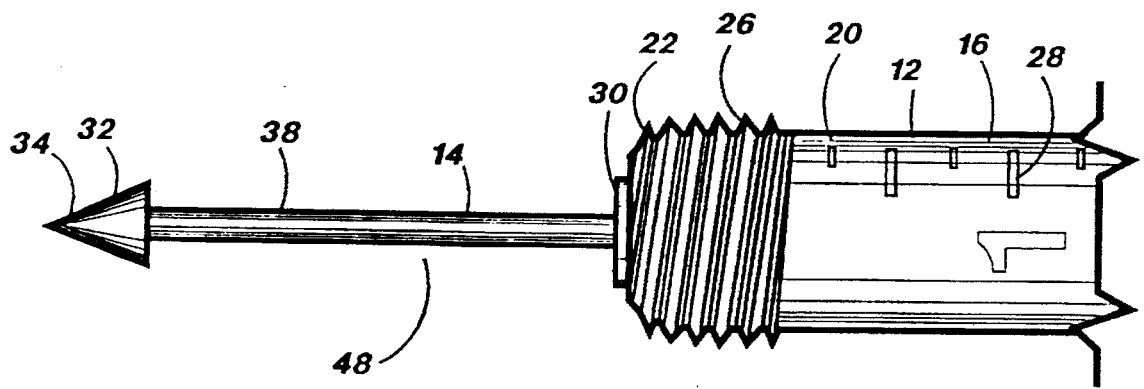
FIG. 8 is a side elevational view of a third alternative embodiment of the bioptic device of the present invention wherein only the cannula tip bears threading.

FIG. 8 illustrates an alternative embodiment wherein the cylindrical section 36 of the stylet tip 32 is omitted and only the needle-like conic section 34 is retained. The threading 40 and 42 on the stylet tip 32 and stylet neck 38 are similarly omitted, but the leading edge 22 of the cannula 12 includes threading 26. The stylet 14 of this embodiment functions in a manner similar to the stylets of the bioptic devices of the prior art, but the threading 26 allows the leading edge 22 of the cannula 12 to fix the tissue to be sampled. In this embodiment, only the cannula 12 is "anchored" to the tissue to be sampled, and it provides the sole means for fixing tissue.

Figure 9:
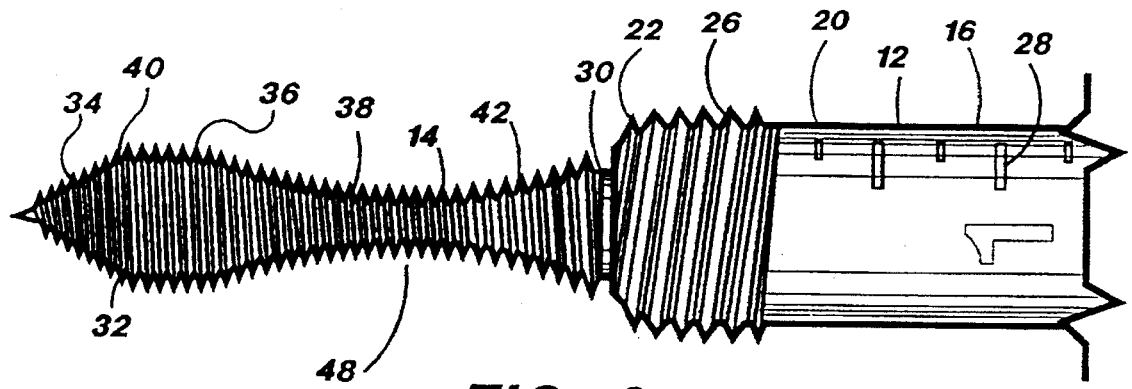
FIG. 9 is a side elevational view of a fourth alternative embodiment of the bioptic device of the present invention wherein the neck is in the shape of a Hindley screw.

FIG. 9 illustrates an alternative embodiment of the bioptic device 10 wherein the stylet neck 38 is in the form of a Hindley screw so that the gutter 48 has an arcuate shape. The advantage of this embodiment is that the gutter 48 has rounded corners where the stylet tip 32 meets the stylet neck 38 and where the stylet neck 38 meets the stylet body 30, making it easier for tissue to flow into the gutter around these corners. This embodiment is extremely effective in fixing tissue within the gutter 48 because the tissue initially fixed by the threading 40 on the stylet tip 32 is "passed" directly to the threading 42 in the gutter 48, ensuring that the gutter 48 will always be filled with tissue. This effect is further enhanced by the use of threading with high grasping effectiveness on the stylet tip 32 and neck 38, such as buttress threading and/or undercut types of threading.

It is contemplated that different types of threading with different pitches, depths, thread angles, and major and minor diameters may be used on different parts of the bioptic device 10 to optimize its performance. The threading may be differed on different parts of the bioptic device 10 depending on the degree of gripping power, tissue collection ability, and trauma reduction the operator wishes to obtain. For example, the leading edge 22 of the cannula 12 may use sharp V threading with a low major diameter and depth so that trauma created by insertion of the cannula 12 is minimized, and so that the leading edge 22 has high gripping ability as the cannula 12 is rotated to drive it forward. The stylet tip 32 may use buttress threading for higher gripping power. The stylet neck 38 may use undercut buttress threading so that the tissue is both tightly gripped and also pulled inward towards the central axis of the stylet 14, increasing the likelihood that the gutter 48 will be entirely filled with tissue.

Figure 10:
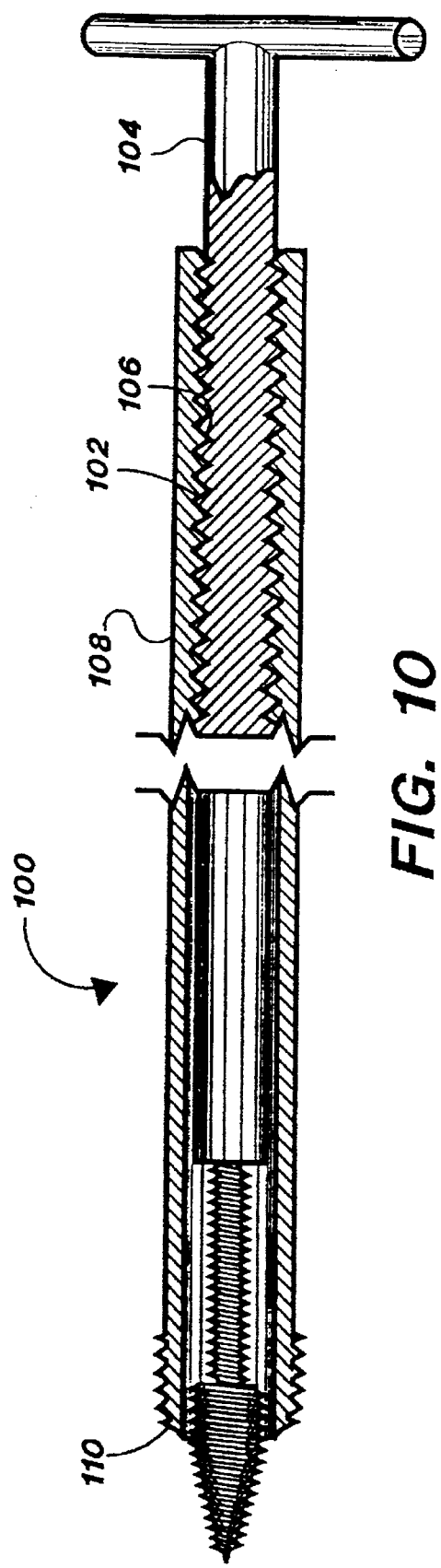
FIG. 10 is a side elevational view of a fifth alternative embodiment of the bioptic device of the present invention, shown with the cannula and a portion of the stylet in cross-section to illustrate the interaction of threading on the cannula and stylet.

FIG. 10 illustrates another alternative embodiment of the bioptic device of the present invention. In this embodiment, the bioptic device 100 includes threading 102 on a portion of the external surface of the stylet 104 and complementary internal threading 106 on the interior surface of the cannula 108. By providing such threading, the stylet 104 cannot be advanced independently of the cannula 108 (and vice versa) except by rotating it. Because the stylet 104 and/or cannula 108 may only be slowly advanced within the body by rotational actuation, there is less likelihood that the bioptic device 100 could be accidentally driven into areas in the body of tissue that are not intended to be sampled. This overcomes the disadvantage of the prior art devices which utilize pushing or thrusting of the stylet and cannula to obtain a tissue sample, and which often cause injury when the tissue to be sampled is missed. Additionally, because the operator is required to slowly rotate the cannula 108 over the stylet 104, the operator's concentration is more focused on the bioptic device 100 than it would be on a prior art bioptic device which is actuated with a quick pushing or thrusting motion. As a result, there is lesser likelihood that the operator will try to obtain a tissue sample by retracting the stylet 104 instead of advancing the cannula 108. Further, since the cannula 108 must be rotated over the stylet 104, the leading edge 110 of the cannula 108 must necessarily apply a shear-style cut.

Yet another alternative embodiment is especially adapted for hard tissue biopsies, e.g., bone biopsies. In this embodiment, the cannula 12 may bear teeth along all or a portion of the leading edge 22, either replacing the threading 26 or being used in conjunction with such threading 26. The teeth may be configured similarly to the teeth commonly seen on surgical saws and medical cutting devices known to the art. Additionally, if desired, the teeth may include side clearance, e.g., the teeth may be spring-set or swage-set. Expansion slots may be provided and may run from the leading edge 22 of the cannula 12 in a generally axial direction along its body 16 to allow the cannula 12 to compress (or expand) radially to reduce the stress on the hard tissue being sampled.

In the hard tissue embodiment described above, the bioptic device 10 is actuated in standard fashion, but the teeth allow the cannula 12 to be rotationally actuated to more easily cut a plug of hard tissue. The stylet 14 is rotationally advanced on the tissue, and the cannula 12 is then also rotationally advanced to follow the stylet 14. After the cannula 12 has cut a plug in the hard tissue, the stylet 14 may be withdrawn through the cannula 12 to pull the plug through the body 16 of the cannula 12 and out the cannula end 24. If the hard tissue being sampled is bone, the cannula 12 may then be used for aspiration of bone marrow. As an alternative mode of operation, the stylet 14 may instead be rotationally advanced on the hard tissue to merely fix the tissue at a desired precise area so that the cannula 12 is certain to sample only this area. The stylet 14 may then be withdrawn after the cannula 12 enters the desired area, and replaced with a different device if desired. It should be noted that the inclusion of teeth at the leading edge 22 is helpful for the sampling of dense tissue, such as hard tumor tissue, and not merely for the sampling of bone.

While the bioptic device of the present invention has been illustrated with a handle 44 for manual actuation of the bioptic device, it is understood that the bioptic device could instead be driven by a motor or similar actuation means, such as that shown in U.S. Pat. No. 4,461,305 to Cibley. These actuation means could require the device to operate with a set order of operational steps, thereby further reducing the risk of operating the device with an erroneous order of operational steps. Additionally, it is understood that the bioptic device of the present invention can incorporate means for locking the cannula to the stylet when the operator wishes to prevent them from moving relative to each other. Examples of such locking means are illustrated in U.S. Pat. No. 769,829 to Mott and U.S. Pat. No. 4,010,737 to Vilaghy et al., each of which utilizes a screw which extends through the cannula and engages the stylet.

The bioptic device is preferably made of a corrosion-resistant, sterilizable metal which retains a cutting edge, such as stainless steel. However, it is possible that the bioptic device could also be made of ceramic, plastic, or composite materials.

It is understood that the invention is not limited to the particular construction and/or arrangement of parts and procedural steps described above, but embraces such modified forms thereof that come within the scope of the following claims.

What is claimed is:

1. A bioptic device comprising:
   a. a cannula including a sharp leading edge;
   b. a stylet adapted to fit within the cannula, the stylet including a stylet tip, a threaded stylet neck adjacent the stylet tip, and a stylet body adjacent the stylet neck, wherein the stylet neck has a smaller minor diameter than the stylet tip and stylet body and the major diameter of the threading on the stylet neck is less than or substantially equal to the maximum diameter of the stylet tip.

2. The bioptic device of claim 1 wherein the leading edge of the cannula is threaded.

3. The bioptic device of claim 1 wherein the leading edge of the cannula includes teeth.

4. A bioptic device comprising:
   a. a cannula including a sharp leading edge;
   b. a stylet adapted to fit within the cannula, the stylet including a stylet tip, a threaded stylet neck adjacent the stylet tip, and a stylet body adjacent the stylet neck, wherein the major diameter of the stylet neck is less than or equal to the stylet tip and stylet body.

5. The bioptic device of claim 4 wherein the major diameter of the threading on the stylet neck is equal to the maximum diameter of the stylet tip.

6. The bioptic device of claim 4 wherein the stylet neck defines a Hindley screw.

7. The bioptic device of claim 4 wherein at least a portion of the stylet tip is threaded.

8. The bioptic device of claim 4 wherein the leading edge of the cannula is threaded.

9. The bioptic device of claim 4 wherein the leading edge of the cannula includes teeth.

10. The bioptic device of claim 4 further comprising internal threading within at least a portion of the cannula and external threading upon at least a portion of the stylet body, wherein the internal threading engages the external threading to allow the stylet to be rotationally advanced and retracted within the cannula.

11. A bioptic device comprising:
    a. a cannula including a sharp leading edge;
    b. a stylet adapted to fit within the cannula wherein the stylet includes a sharpened stylet tip, a threaded stylet neck adjacent the stylet tip, and a stylet body adjacent the stylet tip, wherein the stylet neck has a smaller diameter than the stylet tip and stylet body, and further wherein the stylet neck defines a Hindley screw.

12. The bioptic device of claim 11 wherein the threaded stylet neck utilizes one of the following threading types: American National threading, unified (external) threading, metric threading, sharp V threading, Whitworth standard threading, Acme threading, knuckle threading, square threading, standard worm threading, buttress threading, or undercut buttress threading.

13. The bioptic device of claim 16 wherein the leading edge of the cannula is threaded.

14. The bioptic device of claim 13 wherein the threading on the leading edge is of a different threading type than the threading on the stylet neck.

15. The bioptic device of claim 11 wherein at least a portion of the stylet tip is threaded.

16. The bioptic device of claim 15 wherein the threading on the stylet neck is of a different threading type than the threading on the stylet tip.

17. The bioptic device of claim 2 wherein the threading on the leading edge is of a different threading type than the threading on the stylet neck.

18. The bioptic device of claim 1 wherein at least a portion of the stylet tip is threaded.

19. The bioptic device of claim 18 wherein the threading on the stylet neck is of a different type than the threading on the stylet tip.

20. The bioptic device of claim 4 wherein the threading on the stylet neck utilizes buttress threading.

21. The bioptic device of claim 4 wherein the threading on the stylet neck utilizes undercut threading.

22. The bioptic device of claim 4 wherein at least one of the cannula and stylet bears distance indicia.

23. The bioptic device of claim 7 wherein the threading on the stylet neck is of a different type than the threading on the stylet tip.

24. The bioptic device of claim 8 wherein the threading on the stylet neck is of a different type than the threading on the leading edge of the cannula.

* * * * *